(12) United States Patent
Heresco-Levy et al.

(10) Patent No.: US 8,629,105 B2
(45) Date of Patent: *Jan. 14, 2014

(54) PHARMACEUTICAL COMPOSITIONS FOR THE TREATMENT OF MOVEMENT DISORDERS

(75) Inventors: Uriel Heresco-Levy, Jerusalem (IL); Daniel C. Javitt, Bardonia, NY (US)

(73) Assignee: Sarah Herzog Memorial Hospital Ezrat Nashim Association, Jerusalem (IL)

( * ) Notice: Subject to any disclaimer, the term of this patent is extended or adjusted under 35 U.S.C. 154(b) by 562 days.

This patent is subject to a terminal disclaimer.

(21) Appl. No.: 10/744,452

(22) Filed: Dec. 23, 2003

(65) Prior Publication Data

US 2004/0157926 A1  Aug. 12, 2004

(30) Foreign Application Priority Data

Feb. 6, 2003  (IL) .......................... 154,318

(51) Int. Cl.
*A61K 38/18* (2006.01)
*A61P 13/06* (2006.01)
*A01N 37/12* (2006.01)

(52) U.S. Cl.
USPC .................. 514/8; 514/12; 514/561

(58) Field of Classification Search
USPC ............................. 514/8, 12, 561
See application file for complete search history.

(56) References Cited

U.S. PATENT DOCUMENTS

| | | | | |
|---|---|---|---|---|
| 3,795,738 A | * | 3/1974 | Plotnikoff | 514/19 |
| 3,851,055 A | | 11/1974 | Cavanaugh | |
| 4,966,915 A | * | 10/1990 | Tsuchiya et al. | 514/531 |
| 5,668,117 A | * | 9/1997 | Shapiro | 514/55 |
| 5,837,730 A | * | 11/1998 | Javitt | 514/551 |
| 6,083,941 A | * | 7/2000 | Farb | 514/177 |
| 6,228,875 B1 | * | 5/2001 | Tsai et al. | 514/380 |
| 6,310,085 B1 | * | 10/2001 | Willis | 514/415 |
| 6,361,957 B1 | * | 3/2002 | Javitt | 435/7.1 |
| 6,506,780 B2 | | 1/2003 | Lowe, III | |
| 6,514,973 B1 | * | 2/2003 | Buchholz et al. | 514/249 |
| 6,551,993 B1 | * | 4/2003 | Schneider | 514/17.3 |
| 7,160,913 B2 | * | 1/2007 | Schneider | 514/380 |

OTHER PUBLICATIONS

Tsai et al., Brief reports Am. J. Psych 166: 11(1999).*
Naglak et al., Pediatric Research vol. 24 (1998) 9-13.*
http://www.aminoacidpower.com/osc/product 3 pages 2002.*
Heresco-Levy et al., Archives Gen. Psychiatry vol. 56, 29-26 (1999).*
Savelli et al. Brain Research 682 (1995) 41-49.*
Parson et al. (J. Pharmacology and Experimental Therapeutics 283:1264-1275).*
Samii et al. Brain (1999), 122, 417-425.*
Moris Phy Ther (2000); 80:578-597.*
Webminister II New Riverside University Dictionary (1994) 3pages.*
Uriel Heresco-Levy et al., Efficacy of High-Dose Glycine in the Treatment of Enduring Negative Symptoms of Schizophrenia, Archives of General Psychiatry, Jan. 1, 1999, p. 29-36, vol. 56, No. 1.

* cited by examiner

*Primary Examiner* — Shirley V Gembeh
(74) *Attorney, Agent, or Firm* — Bachman & LaPointe, P.C.

(57) ABSTRACT

The invention provides a pharmaceutical composition, medical food, dietary supplement or micronutrient for the treatment of a movement disorder comprising an NMDAR agonist or partial agonist as active ingredient therein in combination with a pharmaceutically acceptable carrier.

9 Claims, No Drawings

PHARMACEUTICAL COMPOSITIONS FOR THE TREATMENT OF MOVEMENT DISORDERS

The present invention relates to pharmaceutical compositions for the treatment of movement disorders. More particularly, the present invention relates to the use of N-methyl-D-aspartate type glutamate receptor (NMDAR) agonists (NMDAR agonists, also known as NMDA agonists) and partial agonists for the treatment of movement disorders such as Parkinsons disease.

NMDAR are a type of receptor for the excitatory neurotransmitter glutamate. MDAR contain additional modulatory sites, including the following: glycine binding site, polyamine binding site, redox site, Zinc (Zn) site, phosphorylation sites, post-synaptic membrane docking sites and protein-protein interaction sites (e.g., Lynch and Guttman, 2001). The glycine binding site is sensitive to monocarboxyllic amino acids including the endogenous amino acids glycineD-serine and D-alanine. Glycine is synthesized via serine or threonine by serine hydroxymethyltransferase. Synaptic glycine concentrations are regulated by type 1 (GLYT1) and type 2 (GLYT2) glycine transporters, as well as by other amino acid transporters belonging to Systems A, L, ASC, and N (Sershen et al., 1979). GLYT1 transport inhibitors, such as N[3-(4'-fluorophenyl )-3-(4'-phenylphenoxy)propyl]sarcosine (NFPS), potentiate NMDAR activity in vivo, (Bergeron et al., 1989; Klitenick et al., 2001) suggesting a critical role for glycine transporters in NMDAR regulation. Methylated glycine derivates (e.g., methylglycine, sarcosine) may serve as non-specific glycine transport inhibitors D-serine and D-alanine are metabolized by D-amino acid oxidase (DAAO), which is localized particularly in hindbrain. Further, DAAO is regulated by a novel protein termed G72, which may affect metabolic activity of the DAAO enzyme (Chumakov et al., 2002). Glycine, D-serine and D-alanine levels in brain may be modulated by administering exogenous compound (i.e., glycine, D-serine or D-alanine), or naturally occurring precursors to these compounds including but not limited to L-serine, L-phosphoserine, D-phosphoserine and threonine, or by modulation of the synthetic enzymes serine hydroxymethyltransferase or serine racemase. D-Serine or D-alanine levels may also be increased by modulation inhibiting D-serine or D-alanine breakdown, for example, by antagonizing DAAO activity either directly or indirectly (e.g., via modulatory proteins).

Parkinsons disease is neurological disorder characterized by movement disturbances related to extrapyramidal system dysfunction. Key symptoms of Parkinsons disease include tremor, rigidity, dystonia, bradykinesia and akinesia. The primary current treatments for Parkinsons disease include anticholinergics, L-dopa and MAO inhibitors. Dyskinesia is a long-term consequence of antiParkinsonian treatment. Parkinsons disease may occur under several conditions, including 1) idiopathically, 2) as a result of exposure to environmental toxins, particularly those affecting the dopamine system (e.g., 6-OH dopamine, MPTP) or 3) during treatment with antidopaminergic agents, particularly in connection with schizophrenia. Parkinsonian side effects are particularly common during treatment using typical antipsychotic agents such as, but not limited to, haloperidol, flupenazine or chlorpromazine. More recently developed atypical antipsychotics such as olanzapine, risperidone, quetiapine, ziprasidone and aripiprazole are associated with decreased rates of Parkinsonian symptoms. Significant Parkinsonian symptoms also occur spontaneously in up to 20% of individuals with schizophrenia. In general, agents effective in treatment of drug-induced Parkinsonian symptoms, such as anticholinergics and amantadine, are also effective in treatment of idiopathic Parkinsons disease. Symptoms of Parkinsons disease may be evaluated using the Simpson Angus Scale (SAS, Simpson & Angus, 1970) or similar instrument.

Dyskinesias are abnormal movements characterized by having a snakelike or writhing character. Dyskinesias may occur as a consequence of neurological disease such as Huntington's chorea, as a result of damage to specific brain regions such as corpus striatum or subthalamic nucleus, or as a consequence of medical conditions (e.g., Syndenham's chorea), but may also occur as a consequence of long-term exposure to antipsychotic medication. Tardive dyskinesia (TD) is a form of dyskinesia that results from long-term exposure to antipsychotics such as chlorpromazine or haloperidol. TD occurs less frequently following treatment with newer antipsychotics, and symptoms of TD can be suppressed by clozapine. Symptoms of TD are evaluated using instruments such as the Abnormal Involuntary Movement Scale (AIMS, Guy, 1976).

Tics are sudden, rapid, recurrent, nonrhythmic stereotyped movements or vocalizations. Examples of tic disorders include Tourette's disorder, Chronic Motor or Vocal Tic Disorder, Transient Tic Disorder and Tic Disorder Not Otherwise Specified. Tourette's disorder is inherited in an autosomal dominant fashion, which penetrance of approximately 70% in females and 99% in males (DSM-IV, 1994, p. 100). Obsessive compulsive disorder is a disorder characterized by recurrent obsessions or compulsions, leading often to repetitive motor behaviors (e.g., hand washing, ordering, checking) or mental acts (e.g., praying, counting, repeating words silently) (DSM-IV, 1994, p. 418). Obsessive-compulsive disorder is common in patients with Tourette's disorder. Conversely, 20-30% of individuals with Obsessive-Compulsive disorder have reported current or past tics. Etiology of tic disorders and obsessive compulsive disorder are unknown, but may involve autoimmune factors (Hallet et al., 2000), serotonergic dysfunction (e.g., Dursun et al., 1996), or gene expression abnormalities (Greer et al., 2002). Nevertheless, NMDAR may play a critical role in regulation of circuits involved in movement disorders, as NMDAR antagonists worsen symptoms in animal models of the disorder (McGrath et al., 2000).

Although the primary pathology in Parkinsons disease is a loss of dopaminergic neurons in the substantia nigra and ventral tegmental areas, expression of symptoms is the result of interactions between multiple populations of dopaminergic, glutamatergic and GABAergic neurons within the extrapyramidal system. Many neurons involved in the pathophysiology of Parkinsons disease express additional transmitters, including enkephalin (ENK), substance P (SP), somatostatin (SOM), opioids, adenosine, and acetylcholine (ACh). Key structures that may be involved in Parkinsons disease include the nigrostiatal, mesolimbic and mesocortical dopaminegic systems, the basal ganglia including corpus striatum, caudate, putamen and globus pallidus, the subthalamic nuclei, cerebral cortex, cerebellum and portions of thalamus.

NMDAR play a key role in the regulation of movement and striatal function. NMDARs are found on multiple classes of neuron within striatum including projection neurons and internuerons. NMDARs are composed of multiple subunits including an NR1 subunit which is present in virtually all functional NMDARs, and NR2 subunits that are present in variable proportions. Four NR2 subunits (NR2A-D) have been described. NR2A expression is high in GABAergic neurons that express the marker GAD67, intermediate over SP neurons, low in ENK neurons, not found in cholinergic and SOM neurons. In contrast, NR2B expression is intense in all populations of neurons, while expression of NR2C,D is weak (Kuppenbender et al., 2000). The existence of multiple subforms of NMDAR in striatum is supported by the observation that NMDARs controlling GABA and DA release are less sensitive to NMDA than receptors controlling spermidine or ACh release (Nankai et al., 1995).

Current theories of Parkinsons disease postulate an important role of NMDAR in the networks subserving development of Parkinsonian symptoms. However, based upon the clinical observation that amantadine, a widely used anti-Parkinsonian agent, has NMDAR antagonist (as opposed to agonist) properties, it has been suggested that NMDAR antagonists may be beneficial in treating movement disorders. Other findings, such as the ability of glycine antagonists to increase locomotion in monoamine-depleted mice (Slusher et al., 1994) have also been used to teach use of NMDAR antagonists in the treatment of Parkinsons disease. Thus e.g. the literature is replete with references such as U.S. Pat. No. 6,284,774 which teach the use of NMDA receptor antagonists for the treatment of Parkinsons disease.

In contradistinction to the teachings of the prior art it has now been surprisingly found that NMDA receptor agonists, particularly those that target the NMDAR-associated glycine binding site are effective for the treatment of movement disorders such as Parkinsons disease.

NMDAR agonists described in the present application, including glycine and D-serine, are naturally occurring compounds that may be marketed as pharmaceuticals, medical foods or dietary supplements. Previous applications (e.g., U.S. Pat. No. 6,228,875) have described and claimed use of NMDAR agonists only as pharmaceuticals. In contrast, the present application teaches use as medical foods or dietary supplements as well as pharmaceuticals. Thus according to the present invention there is now provided a pharmaceutical composition, medical food or dietary supplement for the treatment of a movement disorder comprising an NMDAR agonist or partial agonist as active ingredient therein in combination with a pharmaceutically acceptable carrier.

The present invention also provides for the use of an NMDAR agonist or partial agonist in the manufacture of a pharmaceutical composition, medical food, or dietary supplement for the treatment of a movement disorder and especially for the treatment of antipsychotic-induced movement disorders and Parkinsons disease.

Prior literature regarding use of NMDAR agonists (as opposed to antagonists) in treatment of Parkinsons disease is minimal. Casey and Shiigi (1999) showed that administration of ketamine induces bradykinesia, dystonia and salivation in neuroleptic sensitized monkeys (Shiigi and Casey, 1999), suggesting that NMDA dysfunction might contribute to symptoms. Schneider et al. (Brain Res 860:190-4, 1991) demonstrated that low dose (320 or 1000 mg/kg) D-cycloserine significantly improved variable delayed-response task (VDR) performance in MPTP-treated monkeys but did not show improvement in bradykinesia, tremor or other core Parkinsonian symptoms (Schneider et al., Brain Res 860:190-4, 1991).

In U.S. Pat. No. 6,228,875 there is described and claimed methods and pharmaceutical compositions for treating neuropsychiatric disorders such as schizophrenia, Alzheimer's Disease, autism, depression, benign forgetfulness, childhood learning disorders, close head injury, and attention deficit disorder using at least one agonist of the glycine site of an NMDA receptor however said patent neither teaches nor suggests that such agonists are effective for the treatment of movement disorders such as Parkinsons disease.

The present findings are also not anticipated by subsequent articles relating to the examples in Tsai and Coyle '875. As shown in Table 2 of Tsai et al., 1998, a paper relating to '875, patients participating in studies disclosed in '875 had minimal levels of pretreatment Parkinsonian symptoms as measured by the SAS (1.4±1.4 points) and dyskinetic symptoms as measured by the AIMS (0.3±0.7 points). Because of patients recruited for that study, therefore, Tsai and Coyle were unable to assess effects of NMDA agonists on movement disorders in general or on Parkinsonian and dyskinetic symptoms in particular. A subsequent study (Tsai et al., 1999) also did not find significant change in SAS or AIMS scores during treatment with D-serine combined with clozapine. In Tsai and Coyle '875, data are presented also with D-alanine and N-methylglycine. In these cases also, no significant changes in SAS or AIMS scores were observed, due in part to low baseline levels. Therefore, neither Tsai and Coyle '875 nor related references teach use of NMDA agonists or partial agonists in treatment of movement disorders or movement-related side effects of antipsychotic medication. In a prior study of glycine (Heresco-Levy et al., 1999, Table 3), SAS scores declined from 1.3 to 0.6 points during glycine treatment vs. no change during placebo. AIMS scores declined from 1.9 to 1.4 during glycine but increased during placebo. Nevertheless, in that study, change scores for SAS and AIMS were not significant for glycine vs. placebo (p>0.02 for both). Thus, the present results are not anticipated by '875 or continuations thereof.

In prior studies of schizophrenia, we and others have demonstrated improvement in negative symptoms during treatment with the NMDAR agonists glycine (Heresco-Levy et al., 1999a; Javitt et al., 2000; Heresco-Levy et al., submitted), D-serine (Tsai et al., 1999) and D-cycloserine (Heresco-Levy et al., 1998; Goff et al., 1999; Heresco-Levy et al., 1999b). Several negative symptoms, including motor retardation and affective blunting resemble symptoms of Parkinsons disease. Nevertheless, these studies did not show significant improvement of motor symptoms during treatment with NMDAR agonists or the partial agonist D-cycloserine, and did not teach use of NMDAR agonists in treatment of movement disorders.

The mechanism by which NMDAR agonists or partial agonists ameliorate symptoms of movement disorder remain to be determined. One potential explanation, however, is that subpopulations of NMDAR may contribute differentially to both pathogenesis and therapeutics. Thus, in terms of pathogenesis, NR2B receptors in striatum have been specifically implicated (Nash & Brotchie, 2002). Further, agents that have shown greatest preliminary effectiveness in Parkinsons disease are all NR2B antagonists (Nikam & Meltzer, 2002). In monkeys, NR2A and NR2B selective antagonists were observed to have differential effects, with the NR2A antagonist MDL 100,453 worsening symptoms of dyskinesia (Woodward et al., 1999). NR2B receptors have numerically lower affinity for glycine than NR2A receptors, and so may be saturated under physiological conditions. Administration of NMDAR agonists such as glycine and D-serine and the NMDA partial agonist D-cycloserine may therefore selectively active NR2A receptors. Activation of NR2A vs. NR2B receptors by NMDAR agonists and partial agonists may, therefore, restore the balance between NR2A and NR2B containing receptors similarly and additively to the effects of NR2B antagonists.

The finding that NMDAR agonists improve antipsychotic-induced movement disorders including Parkinsoriism and TD is not anticipated by prior literature. These findings moreover indicate that NMDAR agonists may be effective in treatment of other movement disorders, including Parkinsons disease, dyskinetic disorders, obsessive-compulsive disorder, tic disorders etc.

While the invention will now be described in connection with certain preferred embodiments in the following examples so that aspects thereof may be more fully understood and appreciated, it is not intended to limit the invention to these particular embodiments. On the contrary, it is intended to cover all alternatives, modifications and equivalents as may be included within the scope of the invention as defined by the appended claims. Thus, the following examples which include preferred embodiments will serve to illustrate the practice of this invention, it being understood that the particulars shown are by way of example and for purposes of illustrative discussion of preferred embodiments of the present invention only and are presented in the cause of providing what is believed to be the most useful and readily understood description of formulation procedures as well as of the principles and conceptual aspects of the invention.

EXAMPLE 1

Beneficial Effects of High Dose Glycine (60 g/d) on EPS and TD in Schizophrenia

Methods:

The study was approved by the appropriate institutional review boards. Seventeen stable inpatients meeting DSM-IV criteria for schizophrenia and free of other axis I diagnoses or significant medical illness were enrolled in the study. Diagnosis was established on the basis of semistructured psychiatric interviews, review of all available medical records, and confirmation by two board-certified psychiatrists. Patients fulfilled criteria for treatment resistance used in previous trials of glycine and had been receiving stable doses of olanzapine or risperidone for at least 3 months before study entry. Medication doses remained fixed throughout the study.

After complete description of the study, written informed consent was obtained from all participating patients. The double-blind, placebo-controlled, crossover study consisted of two random-order 6-week treatment arms (glycine 0.8 g/kg/day, or placebo), separated by a 2-week adjuvant treatment washout. Patients were assessed biweekly with the Positive and Negative Syndrome Scale (PANSS), Brief Psychiatric Rating Scale (BPRS), Simpson-Angus Rating Scale (SAS), and Abnormal Involuntary Movement Scale (AIMS) performed by one trained research psychiatrist, as previously described (3). CBC and SMA-20 measures were assessed biweekly throughout the study. Trough glycine and serine serum levels were assessed at baseline and at the end of the two treatment phases. Data were analyzed by repeated measures ANOVA with within group factor of study phase (glycine/placebo) and time within study phase (pre/post), and between group factor of treatment order.

Results

Three patients were withdrawn from the study during glycine administration due to non-compliance and mild upper gastrointestinal tract discomfort that ceased following discontinuation of glycine treatment (2 patients). Three of the 14 patients who completed the study were women and 11 were men. Their mean age was 46.5 years (SD=9.6), the mean duration of their illness was 25.8 years (SD=11.0) and the mean duration of their current hospitalization was 3.0 years (SD=3.7). Ten patients were receiving olanzapine (mean daily dose: 14.3 mg (SD=3.1); four patients were receiving risperidone (mean daily dose: 6.2 mg (SD=3.1). Seven patients were randomized to receive placebo during the first treatment phase, eight received glycine. Repeated measures multivariate analyses of variance were performed with within-subject factors of treatment phase (placebo versus glycine) and time within phase (baseline versus week 6) and a between-subjects factor of treatment order.

Analyses demonstrated highly significant, large effect size reductions in PANSS negative and cognitive symptoms and for BPRS total scores (Table 1), indicating significant therapeutic efficacy of glycine. Smaller but still significant improvements were observed for positive symptoms. Treatment effects for negative symptoms remained highly significant ($F=22.2$, $df=1,8$, $p<0.002$) even following covariation for changes in all other PANSS symptom factors.

Significant moderate-effect-size treatment effects were noted for both SAS and AIMS scores that decreased following glycine treatment (Table 1). SAS scores decreased by 1.3 points (18%) during glycine treatment vs. a 0.5 point increase during placebo treatment, the result being statistically significant ($p<0.05$). AIMS scores decreased by 1.0 point (32.2.%) during glycine treatment vs. an 0.3 point increase during placebo treatment, the results being statistically significant ($p<0.02$). This represents the first study to show changes in SAS or AIMS score during treatment with NMDAR agonists.

TABLE 1

Mean (sd) PANSS, BPRS, SAS and AIMS Scores of 14 Inpatients with Treatment-Resistant Schizophrenia During the Addition of Glycine, 0.8 g/kg/day, and Placebo to Olanzapine and Risperidone Treatment[1]

|  | Adjuvant Treatment | Score at Baseline | Score at Week 6 | ANOVA (F, p) | % Change during glycine[2] | Effect size (d) |
| --- | --- | --- | --- | --- | --- | --- |
| PANSS |  |  |  |  |  |  |
| Negative Symptoms | Glycine | 24.6 (4.4) | 20.4 (3.9) | 72.1, | 23.3 (8.4) | 2.1 |
|  | Placebo | 22.0 (3.9) | 23.3 (4.0) | 0.006 | CI: 18-28% |  |
| Positive Symptoms | Glycine | 15.4 (2.2) | 14.0 (1.5) | 7.3, | 11.4 (11.7) | 0.7 |
|  | Placebo | 14.3 (1.1) | 14.7 (1.9) | 0.02 | CI: 5-18% |  |
| Cognitive Symptoms | Glycine | 19.1 (2.8) | 17.9 (3.1) | 11.0, | 9.2 (6.8) | 0.9 |
|  | Placebo | 18.0 (3.4) | 18.6 (2.4) | 0.006 | CI: 5-132% |  |
| Excitement | Glycine | 13.2 (2.1) | 12.0 (1.5) | 13.3, | 10.6 (20.9) | 0.6 |
|  | Placebo | 12.3 (1.6) | 12.9 (2.1) | 0.003 | CI: −2-23 |  |
| Depression | Glycine | 14.4 (3.0) | 13.4 (2.1) | 7.2, | 7.4 (17.1) | 0.7 |
|  | Placebo | 13.3 (2.3) | 14.4 (3.0) | 0.02 | CI: −2-17 |  |

TABLE 1-continued

Mean (sd) PANSS, BPRS, SAS and AIMS Scores of 14 Inpatients with Treatment-Resistant Schizophrenia During the Addition of Glycine, 0.8 g/kg/day, and Placebo to Olanzapine and Risperidone Treatment[1]

|  | Adjuvant Treatment | Score at Baseline | Score at Week 6 | ANOVA (F, p) | % Change during glycine[2] | Effect size (d) |
|---|---|---|---|---|---|---|
| BPRS Total | Glycine | 42.6 (6.0) | 36.6 (4.8) | 35.0, | 13.7 (7.5) | 1.6 |
|  | Placebo | 37.9 (4.6) | 40.4 (6.4) | 0.0001 | CI: 9-18 |  |
| SAS | Glycine | 5.3 (3.3) | 4.0 (3.0) | 4.7, | 17.9 (40.1) | 0.6 |
|  | Placebo | 4.4 (2.7) | 4.9 (3.3) | 0.05 | CI: −5-41 |  |
| AIMS | Glycine | 3.6 (2.0) | 2.6 (7.1) | 7.5, | 32.2 (30.4) | 0.6 |
|  | Placebo | 2.9 (1.6) | 3.2 (2.4) | 0.02 | CI: 15-50 |  |

[1]All patients received both treatments in random order, leading to two treatment phases per subject. Data are collapsed across treatment groups (order). PANSS indicates Positive and Negative Syndrome Scale; BPRS, Brief Psychiatric Rating Scale; SAS, Simpson-Angus Scale for Extrapyramidal Symptoms; AIMS, Abnormal Involuntary Movement Scale.
[2]Data are mean (sd). CI = 95% confidence interval. Calculation of the % change scores takes into account the 1-7 PANSS scoring, with 1 representing absence of symptoms for each item.

EXAMPLE 2

Beneficial Effects of High Dose D-serine (0.03 g/d) on EPS and TD in Schizophrenia Methods: Methods for this study are the same as in example 1, except that D-serine (0.3 g/d=approx. 2.1 g/day) was used for treatment. As previously, outcome was assessed using the PANSS, SAS and AIMS. In addition, the Schedule for Assessement of Negative Symptoms (SANS) was used to provide further assessment of negative symptoms. This represents an interim analysis of an ongoing study. Data were analyzed by between-treatment t-test of change scores during D-serine or placebo treatment. Data are analyzed only from subjects (n=23) who completed both study phases.

Results: As with glycine, D-serine led to highly significant improvements in negative, positive and cognitive symptoms of schizophrenia, similar to reported previously by Tsai et al. (1998). As rated by the SAS, a highly significant 42% decline in Parkinsonian symptoms was observed during D-serine, but not placebo, treatment, leading to a highly significant between group response difference (see Table 2). As rated by the AIMS, a highly significant 50% decline in dyskinetic symptoms was observed during D-serine, but not placebo, treatment, leading to a highly significant between group response difference (see Table 2). These findings are similar to those observed previously with glycine, as detailed in example 1.

TABLE 2

Mean (sd) Positive and Negative Syndrome (PANSS), Simpson Angus (SAS) and Abnormal Involuntary Movement (AIMS) scale scores during D-serine (n = 23) and placebo (n = 22) treatment (crossover design)

|  | Treatment Assignment | Treatment week 0 | Treatment week 6 | Δ symptoms | Between-group difference (t, p) |
|---|---|---|---|---|---|
| PANSS |  |  |  |  |  |
| Positive Symptoms | D-serine | 14.2 ± 2.3 | 13.0 ± 2.3 | −1.2 ± 1.1 | t = 2.90, |
|  | Placebo | 13.7 ± 2.4 | 13.5 ± 2.3 | −0.3 ± 1.2 | p = .006 |
| Negative symptoms | D-serine | 23.9 ± 4.0 | 21.0 ± 3.5 | −2.9 ± 1.9 | t = 4.53, |
|  | Placebo | 22.8 ± 3.5 | 22.5 ± 3.0 | −0.3 ± 1.8 | p < .00001 |
| Cognitive symptoms | D-serine | 18.5 ± 2.2 | 17.1 ± 2.7 | −1.4 ± 1.3 | t = 5.90 |
|  | Placebo | 18.0 ± 2.5 | 18.4 ± 2.1 | 0.4 ± 1.1 | p < 0.0001 |
| Depression | D-serine | 15.3 ± 2.6 | 13.8 ± 2.2 | −1.5 ± 1.8 | t = 4.85, |
|  | Placebo | 14.5 ± 2.6 | 15.1 ± 2.4 | 0.6 ± 1.5 | p < .00001 |
| Excitement | D-serine | 11.6 ± 1.5 | 10.9 ± 1.4 | −0.7 ± 1.2 | t = 1.21, |
|  | Placebo | 11.1 ± 1.6 | 11.0 ± 1.5 | −0.1 ± 1.2 | p = .2 |
| SANS Total (with globals) | D-serine | 60.0 ± 9.3 | 51.9 ± 8.0 | −9.0 ± 54.3 | t = 7.15 |
|  | Placebo | 56.1 ± 10.1 | 56.9 ± 9.4 | 0.9 ± 5.3 | p < .00001 |
| SAS | D-serine | 4.2 ± 1.4 | 2.4 ± 0.8 | −1.8 ± 1.3 | t = 5.66, |
|  | Placebo | 3.7 ± 1.6 | 4.0 ± 1.3 | 0.2 ± 1.1 | p < 00001 |
| AIMS | D-serine | 3.0 ± 0.8 | 1.6 ± 1.2 | −1.4 ± 1.1 | t = 5.51 |
|  | Placebo | 2.5 ± 1.2 | 2.7 ± 0.9 | 0.2 ± 0.9 | p < .00001 |

EXAMPLE 3

Beneficial Effects of the Partial Agonist D-cycloserine

Methods: Methods for this study are the same as in example 1, except that D-cycloserine (50 mg/d) was used for treatment. As previously, outcome was assessed using the PANSS, SAS and AIMS. In addition, the Schedule for Assessement of Negative Symptoms (SANS) was used to provide further assessment of negative symptoms. Data are pooled from two previously published studies (Heresco-Levy et al., 1998, 2002). Because analyses were confirmatory, one-tailed statistics were used throughout.

Results: Significant improvements in positive and negative symptoms and general psychopathology were observed, as previously described. D-cycloserine treatment was associated with a significant reduction in dyskinetic symptoms (t=2.21, p<0.025, one tailed) and a nearly significant improvement in Parkinsonian symptoms (t=1.77, p.=04, one tailed) (Table 3).

TABLE 3

Mean (sd) Positive and Negative Syndrome (PANSS), Simpson Angus (SAS) and Abnormal Involuntary Movement (AIMS) scale scores during D-cycloserine (n = 26) and placebo (n = 28) treatment (crossover design)

| | Treatment Assignment | Week Within Treatment Phase | | Ä symptoms | Between-group difference (t, p) |
|---|---|---|---|---|---|
| | | 0 | 6 | | |
| PANSS | | | | | |
| Positive symptoms | D-cycloserine | 26.7 ± 4.5 | 24.6 ± 4.1 | −2.1 ± 2.6 | t = 3.01, p < .003 |
| | Placebo | 25.8 ± 3.7 | 26 ± 4.2 | 0.1 ± 2.8 | |
| Negative symptoms | D-cycloserine | 34.6 ± 6.2 | 31.4 ± 6.5 | −3.2 ± 2.5 | t = 2.93, p < .003 |
| | Placebo | 33.9 ± 6.9 | 32.6 ± 6.4 | −1.2 ± 2.4 | |
| General Psychopathaology | D-cycloserine | 58.7 ± 8.4 | 53.8 ± 8.2 | −4.9 ± 6.2 | t = 2.70, p < .005 |
| | Placebo | 57.5 ± 8.2 | 57.1 ± 9.5 | −0.4 ± 6.2 | |
| Total Symptoms | D-cycloserine | 120 ± 16.7 | 109.7 ± 15.8 | −10.2 ± 8.9 | t = 3.60, p < .001 |
| | Placebo | 117.2 ± 16.2 | 115.6 ± 17.4 | −1.6 ± 8.8 | |
| SAS | D-cycloserine | 4.3 ± 2.4 | 3.6 ± 2.1 | −0.7 ± 1.7 | t = 1.77 |
| | Placebo | 3.6 ± 2.1 | 3.8 ± 2.2 | 0.2 ± 1.9 | p < .05 |
| AIMS | D-cycloserine | 4.7 ± 3.1 | 3.9 ± 3 | −0.8 ± 1.3 | t = 2.21 |
| | Placebo | 3.9 ± 2.7 | 3.9 ± 2.6 | 0 ± 1.2 | p < .03 |

EXAMPLE 4

Effect of Glycine on Vacuous Chewing Motions in Rodents

Vacuous chewing movements (VCM) are a rodent model of TD (Andreassen et al., 1996). In this model, animals are treated chronically with antipsychotics and their vacuous chewing motions are assessed by observation. This model has been shown to be sensitive to differential effects of typical and atypical antipsychotics and potential anti-dyskinetic agents. This example describes effects of the NMDAR agonist glycine on haloperidol-induced VCM.

Methods and Materials

Subjects

Sprague-Dewley rats (Harlan Laboratories, Jerusalem, Israel) weighing 150 to 170 g. were used. The rats were housed in polycarbonate cages (4 in each cage), maintained under a 12 hour-12 hour dark-light (04.00-16.00 hours) cycle, and were allowed water ad libitum. In order to limit neuroleptic-induced weight gain, the food was restricted to 15 g. pellets per animal per day, as used by Andreassen et al (1996). Rats were weighed biweekly throughout the study. Room temperature was maintained at 22±2° C. All procedures were conducted in accordance with local and international laws for the care and use of laboratory animals.

Protocol and Drugs

For two weeks prior to the first drug injection, animals were handled daily and habituated to the animal colony and the procedures related to drug administration and video recording situation. Subsequently (week 0), rats underwent a behavior video recording session following which they were randomized to a haloperidol treatment and a control group. The rats in the treatment group received an intramuscular injection in the thigh muscles with haloperidol decanoate (Pericate, Unipharm Ltd., Tel Aviv, Israel), 100 mg/ml in sesame oil, at a dose of 0.35 mg/kg. The control rats were similarly injected with an equal volume of phosphate buffered saline (PBS). Twenty-three G hypodermic needles were used for all injections. Subsequently, the haloperidol decanoate and saline injections were repeated every four weeks, for 20 weeks. Additional behavior video recording sessions were performed at weeks 12, 20 and 24 (i.e., 4 weeks after the last (fifth) injection). During the injection procedures, rats were handheld with minimal restraint.

On the basis of the results of the behavior assessment performed 24 weeks after the first haloperidol injection (i.e., baseline day), the haloperidol-treated rats were assigned to 10 subject-each treatment groups having an equal mean frequency of observed VCM episodes. One week later (i.e., test day), the groups reported on here were randomized to receive one intraperitoneal injection with either 0.5 ml PBS (vehicle) or 1.6 g/kg glycine in 0.5 ml PBS. Rats underwent a video recorded behavior assessment session 30-150 minutes following the injection. Two weeks after the test day (i.e., post-test day), the video recorded behavior assessment session was repeated in order to investigate longer-term effects of the experimental treatments.

Behavioral Observations and Statistics

Before experiments were started, the rats were handled and habituated to the behavior observation situation. During videotaping, the rats were kept in a clear perspex cage (13×20.5× 13.5 cm), equipped with mirrors allowing videotaping of the rat from all sides simultaneously. The behavior of the animals was videotaped for 5 minutes after a 1 minute adaptation period in the cage.

A trained observer, unaware of the treatment received by the rats, scored the behavior while watching the videotapes. A VCM episode was defined as a bout of vertical deflections of the lower jaw, which could be accompanied by contractions of the jaw musculature. Statistical analyses were performed using the STATISTICA software package (StatSoft Inc., USA). Student's t-test was used to assess the effects of chronic haloperidol treatment compared to placebo. Analysis of variance (ANOVA) with one between group factor (experimental drug treatment) and one repeated measures factor (baseline day vs. test day vs. post-treatment day) was performed to assess the effects of glycine. The statistical significance of interaction of the between group factor and the repeated measures factor is determined in the STATISTICA software package using the Rao R statistic and the F distribution. Post hoc Newman-Keuls tests were used for comparisons between treatments.

Results

Effects of chronic haloperidol treatment on motor activity

Rats that had received haloperidol for 24 weeks displayed an approximately 4-fold significantly higher number of VCM episodes than rats that had received placebo (t=3.29, df=47, p<0.001) indicating that chronic haloperidol administration induced spontaneous VCM. Furthermore, the number of rearing episodes was significantly lower in the haloperidol-treated group (t=5.2, df=47, p<0.0001). Moreover, mobility in general was significantly reduced in the haloperidol-treated rats. During a 5 minute observation interval, the mean time spend in immobility by the haloperidol-treated rats was 103.2±7.8 seconds, in contrast to 53.0±12.7 seconds spent in immobility by the rats that had received placebo (t=2.9, df=45, p<0.005). Overall, the number of grooming episodes did not differ between haloperidol-treated rats and controls (t=1.4, df=47, p<0.17).

VCM measures were compared on test day between animals receiving vehicle injections and those receiving glycine. One way ANOVA with repeated measures revealed significant interaction of drug and observation day on VCM frequency with Rao R (6,64)=3.44, p<0.005). Post hoc comparisons of VCM frequency at baseline and following GLY administration at the test day further revealed that the administration of GLY resulted in a significant 82% reduction in the number of VCM episodes (p<0.001). Moreover, post hoc comparison of VCM frequencies in the placebo and glycine groups at test day indicated a significantly lower VCM frequency following glycine acute administration (p<0.01). The number of VCM in the glycine-treated groups at baseline and post-test day did not differ significantly (p<0.07), indicating that 2 weeks post-acute GLY administration, VCM levels returned to their previous, pre-experimental treatment levels. These findings, overall, support the clinical observation of decreased VCM following NMDAR agonist treatment.

The examples above demonstrate effectiveness of two full NMDAR agonists, as well as a partial NMDAR agonist in treatment of antipsychotic-induced movement disorder, including Parkinsonian and dyskinetic symptoms. Other methods for augmenting NMDA transmission via the glycine binding site have been proposed including use of glycine transport inhibitors (aka transport antagonists, uptake inhibitors, uptake antagonists), acting at the GLYT1, GLYT2, System A, System ASC or other glycine transport sites, and modulators of D-serine metabolism including inhibitor of b-serine transport and of D-amino acid oxidase. Agents may be screened for effectiveness in stimulating NMDA transmission in vitro using assays, for example, measuring modulation of NMDAR-mediatedactivity in hippocampal slices (Bergeron et al., 1998) or of NMDAR-stimulated dopamine release in isolated mouse striatum (Javitt et al., 2000). Agents may be screened in vivo using assays, for example, measuring amphetamine induced dopamine release or NMDAR-mediated electrophysiological activity (Klitenick et al., 2001). Agents will be effective in ameliorating movement disorders at doses sufficient to potentiate NMDAR-mediated neurotransmission in vivo.

In addition to the embodiments listed above, prodrugs may also be administered. Prodrugs are defined as agents that are not themselves agonists of the NMDAR, but which enter the brain and are converted or metabolized there into effective agonists. An example of a glycine prodrug is milacemide (Doheny et al., 1996). Simple precursors can be made by esterification, alkylation or other linkage (Kao et al., 2000; Schwartz et al., 1991; Toth et al., 1986), most effectively to hydrophobic groups that increase lipophilicity and diffusion into CNS (e.g., Cooper et al., 1987). In a preferred embodiment of the invention, NMDAR agonists, including but not limited to glycine, D-serine, or D-alanine, are conjugated to molecules that are actively transported into the CNS, leading to increased central penetration (e.g., Battaglia et al., 2000; Fernandez et al., 2000; Bonina et al., 1999; Halmos et al., 1997; de Boer et al., 2002; Kido e tal., 2001, Fisher et al., 2002, Rouselle et al., 2002). Precursors to glycine, D-serine or D-alanine, including threonine, L-phosphoserine and D-phosphoserine, may also be incorporated into prodrugs.

The pharmaceutical compositions can be administered to the patient by any, or a combination, of several routes, such as oral, intravenous, trans-mucosal (e.g., nasal, vaginal, etc.), pulmonary, transdermal, ocular, buccal, sublingual, intraperitoneal, intrathecal, intramuscular, or long term depot preparation. Solid compositions for oral administration can contain suitable carriers or excipients, such as corn starch, gelatin, lactose, acacia, sucrose, microcrystalline cellulose, kaolin, mannitol, dicalcium phosphate, calcium carbonate, sodium chloride, lipids, alginic acid, or ingredients for controlled slow release. Disintegrators that can be used include, without limitation, micro-crystalline cellulose, corn starch, sodium starch glycolate and alginic acid. Tablet binders that may be used include, without limitation, acacia, methylcellulose, sodium carboxymethylcellulose, polyvinylpyrrolidone (Povidone), hydroxypropyl methylcellulose, sucrose, starch, and ethylcellulose.

Liquid compositions for oral administration prepared in water or other aqueous vehicles can include solutions, emulsions, syrups, and elixirs containing, together with the active compound(s), wetting agents, sweeteners, coloring agents, and flavoring agents. Various liquid and powder compositions can be prepared by conventional methods for inhalation into the lungs of the patient to be treated.

Injectable compositions may contain various carriers such as vegetable oils, dimethylacetamide, dimethylformamide, ethyl lactate, ethyl carbonate, isopropyl myristate, ethanol, polyols (glycerol, propylene glycol, liquid polyethylene glycol, and the like). For intravenous injections, the compounds may be administered by the drip method, whereby a pharmaceutical composition containing the active compound(s) and a physiologically acceptable excipient is infused. Physiologically acceptable excipients may include, for example, 5% dextrose, 0.9% saline, Ringer's solution or other suitable excipients. For intramuscular preparations, a sterile composition of a suitable soluble salt form of the compound can be dissolved and administered in a pharmaceutical excipient such as Water-for-Injection, 0.9% saline, or 5% glucose solution, or depot forms of the compounds (e.g., decanoate, palmitate, undecylenic, enanthate) can be dissolved in sesame oil. Alternatively, the pharmaceutical composition can be formulated as a chewing gum, lollipop, or the like.

It will be evident to those skilled in the art that the invention is not limited to the details of the foregoing illustrative examples and that the present invention may be embodied in other specific forms without departing from the essential attributes thereof, and it is therefore desired that the present embodiments and examples be considered in all respects as illustrative and not restrictive, reference being made to the appended claims, rather than to the foregoing description, and all changes which come within the meaning and range of equivalency of the claims are therefore intended to be embraced therein.

References

Battaglia G, La Russa M, Bruno V, Arenare L, Ippolito R. Copani A, Bonina F, Nicoletti F. Systemically administered D-glucose conjugates of 7-chlorokynurenic acid are centrally available and exert anticonvulsant activity in rodents. Brain Res 2000;860(1-2):149-56.

Bergeron R, Meyer T M, Coyle J T, Greene R W: Modulation of N-methyl-D-aspartate receptor function by glycine transport. Proc Natl Acad Sci USA 1998; 95(26): 15730-4

Blanchet P J, Konitsiotis S, Whittemore E R, Zhou Z L, Woodward R M, Chase T N: Differing effects of N-methyl-D-aspreceptor subtype selective antagonists on dyskinesias in levodopa-treated 1-methyl-4-phenyl-tetrahydropyridine monkeys. J Pharmacol Exp Ther 1999; 290(3):1034-40

Bonina F P, Arenare L, Palagiano F, Saija A, Nava F, Trombetta D, de Caprariis P. Synthesis, stability, and pharmacological evaluation of nipecotic acid prodrugs. J Pharm Sci 1999;88(5):561-7.

Chumakov I, Blumenfeld M, Guerassimenko O, Cavarec L, Palicio M, Abderrahim H, Bougueleret L, et al. Genetic and physiological data implicating the new human gene G72 and the gene for D-amino acid oxidase in schizophrenia. Proc Natl Acad Sci USA 2002;99(21):13675-80.

Cooper D R, Marrel C, van de Waterbeemd H, Testa B, Jenner P, Marsden C D. L-dopa esters as potential prodrugs: effect on brain concentration of dopamine metabolites in reserpinized mice. J Pharm Pharmacol 1987;39(10):809-18.

De Boer A G, Van Der Sandt I C, Gaillard P J. The Role of Drug Transporters at the Blood-Brain Barrier. Annu Rev Pharmacol Toxicol 2002.

Diagnostic and Statistical Manual of Mental Disorders, 4th edition (DSM-IV). American Psychiatric Press, Washington, D.C. 1994.

Doheny M H, Nagaki S, Patsalos P N. A microdialysis study of glycinamide, glycine and other amino acid neurotransmitters in rat frontal cortex and hippocampus after the administration of milacemide, a glycine pro-drug. Naunyn Schmiedebergs Arch Pharmacol 1996;354(2):157-63.

Dursun S M, Handley S L. Similarities in the pharmacology of spontaneous and DOI-induced head-shakes suggest 5HT2A receptors are active under physiological conditions. Psychopharmacology (Berl) 1996;128(2):198-205.

Fernandez C, Nieto O, Rivas E, Montenegro G, Fontenla J A, Fernandez-Mayoralas A. Synthesis and biological studies of glycosyl dopamine derivatives as potential antiparkinsonian agents. Carbohydr Res 2000;327(4):353-65.

Goff D C, Tsai G, Levitt J, Amico E, Manoach D, Schoenfeld D A, Hayden D L, McCarley R, Coyle J T: A placebo-controlled trial of D-cycloserine added to conventional neuroleptics in patients with schizophrenia. Arch Gen Psychiatry 1999; 56(1):21-7.

Greer J M, Capecchi M R. Hoxb8 is required for normal grooming behavior in mice. Neuron 2002;33(1):23-34.

Guy W, ed. ECDEU Assessment Manual for Psychopharmacology. Washington D.C.: US Department of Health, Education and Welfare; 1976.

Hallett J J, Harling-Berg C J, Knopf P M, Stopa E G, Kiessling L S. Anti-striatal antibodies in Tourette syndrome cause neuronal dysfunction. J Neuroimmunol 2000; 111(1-2):195-202.

Halmos T, Santarromana M, Antonakis K, Scherman D. Synthesis of O-methylsulfonyl derivatives of D-glucose as potential alkylating agents for targeted drug delivery to the brain. Evaluation of their interaction with the human erythrocyte GLUT1 hexose transporter. Carbohydr Res 1997; 299(1-2):15-21.

Heresco-Levy U, Ermilov M, Shimoni J, Shapira B, Silipo G, Javitt D C: Placebo-controlled trial of D-cycloserine added to conventional neuroleptics, olanzapine, or risperidone in schizophrenia. Am J Psychiatry 2002; 159(3):480-2

Heresco-Levy U, Javitt D C, Ermilov M, Mordel C, Silipo G, Lichtenstein M: Efficacy of high-dose glycine in the treatment of enduring negative symptoms of schizophrenia. Arch Gen Psychiatry 1999; 56(1):29-36

Heresco-Levy U, Javitt D C, Ermilov M, Silipo G, Shimoni J: Double-blind, placebo-controlled, crossover trial of D-cycloserine adjuvant therapy for treatment-resistant schizophrenia. Int. J. Neuropsychopharmacol. 1998; 1(2):131-136

Javitt D C, Sershen H, Hashim A, Lajtha A: Inhibition of striatal dopamine release by glycine and glycyldodecylamide. Brain Res Bull 2000; 52(3):213-6

Javitt D C, Silipo G, Cienfuegos A, Shelley A M, Bark N, Park M, Lindenmayer J P, Suckow R, Zukin S R: Adjunctive high-dose glycine in the treatment of schizophrenia. Int J Neuropsychopharmacol 2001; 4(4):385-91

Kido Y, Tamai I, Ohnari A, Sai Y, Kagami T, Nezu J, Nikaido H, Hashimoto N, Asano M, Tsuji A. Functional relevance of carnitine transporter OCTN2 to brain distribution of L-carnitine and acetyl-L-carnitine across the blood-brain barrier. J Neurochem 2001;79(5):959-69.

Klitenick M A, Atkinson B N, Baker D A, Bakker M, Bell S C, Borghys H, Caron M G, Ceuster M, De Coster R, DeVivo M, DelVecchio R A, Draper S, Egle I, Frey J, Calnetdinov R R, Hopper A T, Javitt D C, et al.: Development and characterization of GlyT1-selective glycine reuptake inhibitors, in American College of Neuropsychopharmacology 40th Annual Meeting. Kona, Hi., 2001.

McGrath M J, Campbell K M, Parks C R, Burton F H. Glutamatergic drugs exacerbate symptomatic behavior in a transgenic model of comorbid Tourette's syndrome and obsessive-compulsive disorder. Brain Res 2000;877(1):23-30.

Nash J E, Brotchie J M: Characterisation of striatal NMDARs involved in the generation of parkinsonian symptoms: intrastriatal microinjection studies in the 6-OHDA-lesioned rat. Mov Disord 2002; 17(3):455-66

Nikam S S, Meltzer L T: NR2B selective NMDAR antagonists. Curr Pharm Des 2002; 8(10):845-55

Rousselle C, Clair P, Temsamani J, Scherrmann J M. Improved brain delivery of benzylpenicillin with a peptide-vector-mediated strategy. J Drug Target 2002; 10(4):309-15.

Schwartz B L, Hashtroudi S, Herting R L, Handerson H, Deutsch S I. Glycine prodrug facilitates memory retrieval in humans. Neurology 1991;41:1341-1343.

Sershen H, Lajtha A. Inhibition pattern by analogs indicates the presence of ten or more transport systems for amino acids in brain cells. J Neurochem 1979;32:719-726.

Simpson G M, Angus J W S. A rating scale for extrapyramidal side effects. Acta Psych Scand Suppl. 1970; 212:11-19.

Toth E, Weiss B, Banay-Schwartz M, Lajtha A. Effect of glycine derivatives on behavioral changes induced by 3-mercaptopropionic acid or phencyclidine in mice. Res. Comm. Psychol. Psychiat. Behav. 1986;11:1-9.

Tsai G, Yang P, Chung L C, Lange N, Coyle J T: D-serine added to antipsychotics for the treatment of schizophrenia. Biol Psychiatry 1998; 44(11):1081-9

What is claimed is:

1. A method for the treatment of dyskinetic symptoms in a patient with a movement disorder, comprising:
    identifying a population of patients based upon said patients having at least one movement disorder selected from the group consisting of Huntington's chorea, Wilson disease, Tourette's disease, tic disorders, obsessive-compulsive disorder, akathisia, and dyskinesia, and selecting said patient from the population of patients;
    administering to said patient a therapeutically effective amount of an agonist of the glycine-site of an N-methyl-D-aspartate (NMDA) receptor, wherein said agonist is selected from the group consisting of glycine, d-serine, a glycine uptake inhibitor, a d-serine uptake inhibitor and combinations thereof, so as to alleviate said symptoms,
    wherein glycine is used at a dose of between 15 mg and 150 g per day.

2. The method of claim 1 in which NMDAR agonists are administered at a dose sufficient to augment NMDAR mediated neurotransmission.

3. The method of claim 1, further comprising the step of administering to said patient medications known to be effective in treatment of movement disorders selected from the group consisting of dopaminergic agents, anticholinergics, adenosine modulators and combinations thereof.

4. The method of claim 1, wherein said dyskinesia is tardive dyskinesia.

5. The method of claim 1, further comprising the step of administering to said patient a therapeutically effective amount of sarcosine.

6. The method of claim 1, wherein said movement disorder is selected from the group consisting of Huntington's chorea, Tourette's disease, tic disorders, and obsessive-compulsive disorder.

7. A method for the treatment of dyskinetic symptoms in a patient with a movement disorder, comprising:
    identifying a population of patients based upon said patients having at least one movement disorder selected from the group consisting of Huntington's chorea, Wilson disease, Tourette's disease, tic disorders, obsessive-compulsive disorder, akathisia, and dyskinesia, and selecting said patient from the population of patients;
    administering to said patient a therapeutically effective amount of an agonist of the glycine-site of an N-methyl-D-aspartate (NMDA) receptor, wherein said agonist is selected from the group consisting of glycine, d-serine, a glycine uptake inhibitor, a d-serine uptake inhibitor and combinations thereof, so as to alleviate said symptoms,
    wherein d-serine is used at a dose of 250 mg-20 g per day.

8. The method of claim 3, wherein said dopaminergic agents comprise L-dopa.

9. The method of claim 7, wherein said movement disorder is selected from the group consisting of Huntington's chorea, Tourette's disease, tic disorders, and obsessive-compulsive disorder.

* * * * *